(12) United States Patent
Reber et al.

(10) Patent No.: US 6,727,103 B1
(45) Date of Patent: *Apr. 27, 2004

(54) BINDING ASSAYS

(75) Inventors: William L. Reber, Rollings Meadows, IL (US); Cary D. Perttunen, Shelby Township, MI (US)

(73) Assignee: Amersham Biosciences AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/642,863

(22) Filed: Aug. 21, 2000

Related U.S. Application Data (62) Division of application No. 08/846,907, filed on Apr. 30, 1997, now Pat. No. 6,110,748.

(51) Int. Cl.⁷ .............................................. G01N 33/53
(52) U.S. Cl. .................... 436/518; 435/7.1; 435/6; 435/7.92; 435/7.94; 435/287.2; 436/525; 436/526; 436/805; 436/806; 422/82.05; 422/68.1; 422/82.08; 422/63; 422/66; 422/67; 422/58
(58) Field of Search .................... 435/7.1, 6, 7.92, 435/7.94, 287.2; 436/518, 525, 526, 805, 806; 422/82.05, 68.1, 82.08, 63, 66, 67.58

(56) References Cited

U.S. PATENT DOCUMENTS

| 4,118,280 | A |   | 10/1978 | Charles et al. ............... 195/127 |
| 5,096,670 | A |   | 3/1992  | Harris et al. .................. 422/65 |
| 5,139,744 | A |   | 8/1992  | Kowalski ...................... 422/67 |
| 5,518,923 | A |   | 5/1996  | Berndt et al. ............. 435/287.3 |
| 5,532,128 | A |   | 7/1996  | Eggers et al. ................. 435/16 |
| 5,545,531 | A | * | 8/1996  | Rava et al. |
| 5,565,324 | A |   | 10/1996 | Still et al. ...................... 435/6 |
| 5,653,939 | A |   | 8/1997  | Hollis et al. .................. 422/50 |
| 5,736,332 | A |   | 4/1998  | Mandecki ...................... 435/6 |

OTHER PUBLICATIONS www.labfocus.com/biochem/labfeat.htm—Printed Nov. 1996.
www.labfocus.com/abc/STAFEA.htm—Printed Nov. 1996.
www.awaretech.com/Identi–Link.html—Printed Nov. 1996.
www.sanguin.com/M2000.htm—Printed Nov. 1996.
www.sanguin.com/INFORM.htm—Printed Nov. 1996.
www.packardinst.com/m–probe.htm—Printed Nov. 1996.
www.packardinst.com/mp204–bc.htm—Printed Nov. 1996.
Product Description, Gamera Bioscience Personal.

* cited by examiner

*Primary Examiner*—Bao-Thuy L. Nguyen
(74) *Attorney, Agent, or Firm*—Royal N. Ronning, Jr.

(57) ABSTRACT

In accordance with a first aspect, a binding assay comprises a machine-readable storage medium which supports a molecular receptor (22). In accordance with a second aspect, a support member (50) supports first (22) and second (24) molecular receptors and first (26) and second (28) data identifying the molecular receptors (22,24). In accordance with a third aspect, a support member has a first annular portion (106) to support molecular receptors and a second annular portion (108) to support machine-readable data identifying the plurality of molecular receptors.

19 Claims, 6 Drawing Sheets

BINDING ASSAYS

The present application is a divisional application of U.S. application Ser. No. 08/846,907, filed on Apr. 30, 1997, U.S. Pat. No. 6,110,748, which is hereby incorporated by reference, and priority thereto for common subject matter is hereby claimed.

RELATED APPLICATIONS

The present application is related to the following application:

"Molecular Detection Devices and Methods of Forming Same", Ser. No. 08/846,975, filed Apr. 30, 1997.

The subject matter of the above-listed application is hereby incorporated by reference into the disclosure of the present application.

TECHNICAL FIELD

The present invention relates to molecular detection devices and methods and systems for performing a binding assay therewith.

BACKGROUND OF THE INVENTION

Recent efforts have been directed in developing chips for molecular detection. Of particular interest are DNA chips for sequencing and diagnostic applications. A DNA chip includes an array of chemically-sensitive binding sites having single-stranded DNA probes or like synthetic probes for recognizing respective DNA sequences. The array of binding sites is typically arranged in a rectangular grid.

A sample of single-stranded DNA is applied to the binding sites of the DNA chip. The DNA sample attaches to DNA probes at one or more of the binding sites. The sites at which binding occurs are detected, and one or more molecular structures within the sample are subsequently deduced.

In sequencing applications, a sequence of nucleotide bases within the DNA sample can be determined by detecting which probes have the DNA sample bound thereto. In diagnostic applications, a genomic sample from an individual is screened with respect to a predetermined set of probes to determine if the individual has a disease or a genetic disposition to a disease.

BRIEF DESCRIPTION OF THE DRAWINGS

The invention is pointed out with particularity in the appended claims. However, other features of the invention are described with reference to the following detailed description in conjunction with the accompanying drawings in which:

DETAILED DESCRIPTION OF A PREFERRED EMBODIMENT

Preferred embodiments of the present invention provide binding assays with binding sites arranged either in a circular grid or lattice, or in a spiral grid or lattice on a disk-shaped member. Additionally, the binding assays include machine-readable data to identify the binding sites. These embodiments facilitate both random access to the binding sites, i.e. accessing the binding sites in an arbitrary order, and sequential access to the binding sites. Optionally, the binding assay can include storage media to store data associated with binding events at the binding sites.

Figure 1:
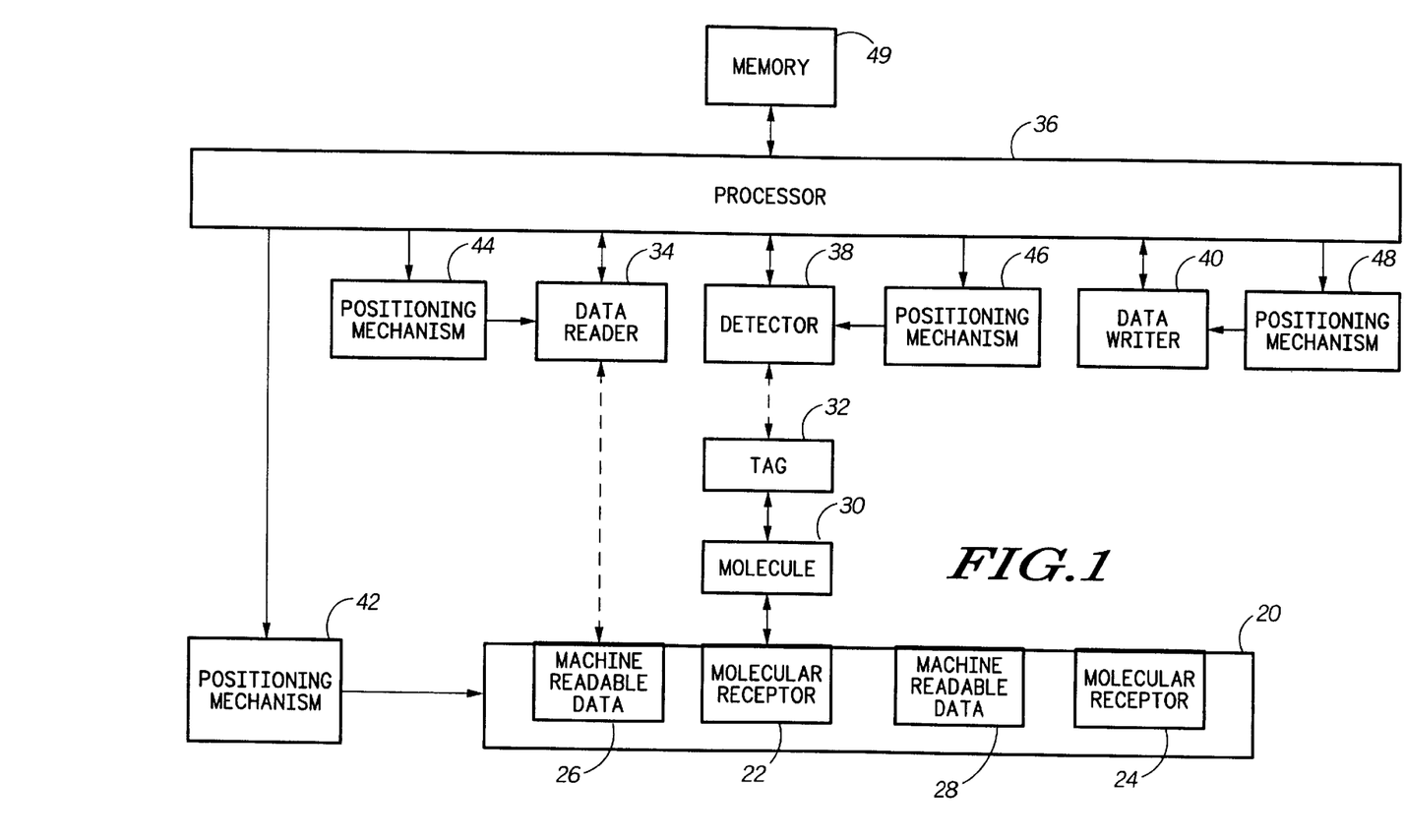
FIG. 1 is a block diagram of an embodiment of a molecular detection system in accordance with the present invention.

FIG. 1 is a block diagram of an embodiment of a molecular detection system in accordance with the present invention. The system includes a device 20 for performing an assay such as a binding assay. The assay can be performed for a variety of applications, including but not limited to, sequencing applications, diagnostic applications, forensic applications, and human-identity applications.

The device 20 has a plurality of molecular receptors including a first molecular receptor 22 and a second molecular receptor 24. Each of the molecular receptors is for binding or hybridizing with a corresponding molecule having a predetermined or preselected structure.

Each molecular receptor can include a biological molecule or synthetic molecules having a specific affinity to its corresponding molecule. For example, each molecular receptor can include a chain of nucleotide bases to hybridize with a molecule having a complementary chain of nucleotide bases. In this case, each molecular receptor can include a DNA probe for detecting a corresponding, complementary DNA base sequence in a sample, or an RNA probe for detecting a corresponding, complementary RNA base sequence in a sample.

Alternatively, each molecular receptor can include a member, such as a film, having an affinity to a corresponding molecule in a sample. For example, each film can be molecular imprinted in accordance with U.S. Pat. No. 5,587,273 to Yan et al., which is hereby incorporated by reference into the present disclosure. In this case, each film is molecularly imprinted using a corresponding imprinting molecule. Other examples of molecular receptors are given in U.S. Pat. Nos. 5,110,833, 5,310,648, 5,372,719, 5,453,199, 5,461,175, and 5,541,342 which are hereby incorporated by reference into the present disclosure.

As another alternative, each molecular receptor can include an imprinted matrix in accordance with U.S. Pat. No. 5,310,648 to Arnold et al., which is hereby incorporated by reference into the present disclosure.

The plurality of molecular receptors are disposed at a plurality of sites of the device 20. With reference to FIG. 1, the first molecular receptor 22 is disposed at a first site, and the second molecular receptor 24 is disposed at a second site. The sites can serve as binding sites, hybridization sites, recognition sites, or molecular detection sites, for example. Although the sites can have any arrangement in general, it is preferred that the sites be arranged along annular or spiral tracks.

The device 20 further includes machine-readable data associated with the molecular receptors. The machine-readable data includes first machine-readable data 26 associated with the first molecular receptor 22, and second machine-readable data 28 associated with the second molecular receptor 24. Preferably, the first machine-readable data 26 identifies the first molecular receptor 22, and the second machine-readable data 28 identifies the second molecular receptor 24.

For example, the first machine-readable data 26 can encode all or a portion of a base sequence associated with the first molecular receptor 22. The base sequence can include a base sequence of a molecule included in the first molecular receptor 22. Alternatively, the base sequence can include a base sequence of a molecule complementary to the first molecular receptor 22. In a similar manner, the second machine-readable data 28 can encode all or a portion of a base sequence associated with the second molecular receptor 24.

As with the sites, it is preferred that the machine-readable data be distributed along annular or spiral tracks. In general, however, the machine-readable data can be disposed in other arrangements.

A sample is applied to the device 20 to perform the binding assay. Examples of the sample include but are not limited to a ligand sample, a nucleic acid sample, a genomic sample from an organism or a plant, and an environmental sample. Of particular interest is where the sample includes a sequence of at least one nucleotide base. In this case, the sample can include at least one polynucleotide molecule such as DNA or RNA.

The molecules in the sample can be tagged with members to assist in the detection of binding events. Such members are commonly referred to in the art as tags, markers, and labels. Examples of such members include, but are not limited to, radioactive members, optical members (such as fluorescent members, luminescent members, and light-scattering members), charged members, and magnetic members.

The sample is allowed to bind or hybridize with the molecular receptors. For purposes of illustration and example, a molecule 30 in the sample binds with the molecular receptor 22. The molecule 30 optionally has a tag 32 associated therewith.

The system includes a data reader 34 for reading the machine-readable data, including the first machine-readable data 26 and the second machine-readable data 28, from the device 20. Dependent on the form of the machine-readable data, the data reader 34 can include a magnetic data reader having a magnetic reading head, or an optical data reader such as a CD-ROM reader or a DVD reader having an optical reading head. The data reader 34 generates a signal associated with machine-readable data read thereby, and communicates the signal to a processor 36.

The system further includes a detector 38 for detecting binding events between sample molecules and the molecular receptors of the device 20. Examples of the detector 38 include but are not limited to an optical detector, a magnetic detector, an electronic detector, a radioactivity detector, or a chemical detector. The detector 38 generates a signal associated with binding events detected thereby, and communicates the signal to the processor 36.

To trim the design, the data reader 34 and the detector 38 can share a common sensor. For example, the data reader 34 and the detector 38 can share a magnetic reading head both to read magnetic machine-readable data and to detect magnetic tags associated with binding events, or an optical reading head both to read optical data and to detect optical indications associated with binding events.

Optionally, the system further includes a data writer 40 for writing data to the device 20. The data can include data associated with binding events as sensed by the detector 38. The data writer 40 can include a magnetic data writer, an optical data writer, or a magnetooptical data writer, for example.

A positioning mechanism 42 positions the device 20 with respect to the data reader 34, the detector 38, and the data writer 40. Depending on the form of the device 20 and the arrangement of the machine-readable data and the molecular receptors, the positioning mechanism 34 can include a rotary positioning mechanism such as a spindle or a turntable, a translational positioning mechanism such as a conveyor, and/or a multiple degree of freedom positioning mechanism such as a robotic arm. In preferred embodiments wherein the device 20 is disk-shaped, the positioning mechanism 42 includes a rotary positioning mechanism such as in a CD-ROM reader or a DVD reader.

A second positioning mechanism 44 positions the data reader 34 with respect to the device 20. Depending on the form of the device 20 and the arrangement of the machine-readable data, the second positioning mechanism 44 can include a rotary positioning mechanism such as a spindle or a turntable, a translational positioning mechanism such as a conveyor, and/or a multiple degree of freedom positioning mechanism such as a robotic arm. In preferred embodiments wherein the device 20 is disk-shaped, the second positioning mechanism 44 includes a translational positioning mechanism which translates a reading head along a radial axis, such as in a CD-ROM reader or a DVD reader.

A third positioning mechanism 46 positions the detector 38 with respect to the device 20. Depending on the form of the device 20 and the arrangement of the binding sites, the third positioning mechanism 46 can include a rotary positioning mechanism such as a spindle or a turntable, a translational positioning mechanism such as a conveyor, and/or a multiple degree of freedom positioning mechanism such as a robotic arm. In preferred embodiments wherein the device 20 is disk-shaped, the third positioning mechanism 46 includes a translational positioning mechanism which translates a detector head along a radial axis.

A fourth positioning mechanism 48 positions the data writer 40 with respect to the device 20. Depending on the form of the device 20 and the arrangement of the machine-readable storage media, the fourth positioning mechanism 48 can include a rotary positioning mechanism such as a spindle or a turntable, a translational positioning mechanism such as a conveyor, and/or a multiple degree of freedom positioning mechanism such as a robotic arm. In preferred embodiments wherein the device 20 is disk-shaped, the fourth positioning mechanism 48 includes a translational positioning mechanism which translates a writing head along a radial axis.

To trim the design, a single positioning mechanism can replace the positioning mechanisms 44, 46, and 48. In this case, the single positioning mechanism positions the data reader 34, the detector 38, and the data writer 40.

The processor 36 directs the operation of the positioning mechanisms 42, 44, 46, and 48, the data reader 34, the detector 38, and the data writer 40 to collect data from a plurality of sites and to write data to the device 20. The processor 36 can direct the operation of the aforementioned components to collect data in a sequential manner or in a random access manner. The processor 36 can include a computer or other like processing apparatus to direct the operation of the system.

The processor 36 can receive signals associated with machine-readable data from the data reader 34 and signals associated with binding data from the detector 38. The processor 36 can store the data in a memory 49 for subsequent retrieval. Optionally, the processor 36 communicates signals to the data writer 40 to write data to the device 20.

The processor 36 can determine a characteristic of the sample based upon the collected data. Examples of determining a characteristic include but are not limited to determining a base sequence associated with the sample (e.g. for sequencing by hybridization), or determining whether a predetermined base sequence is present within the sample (e.g. for diagnostic, forensic, or identity procedures).

Figure 2:
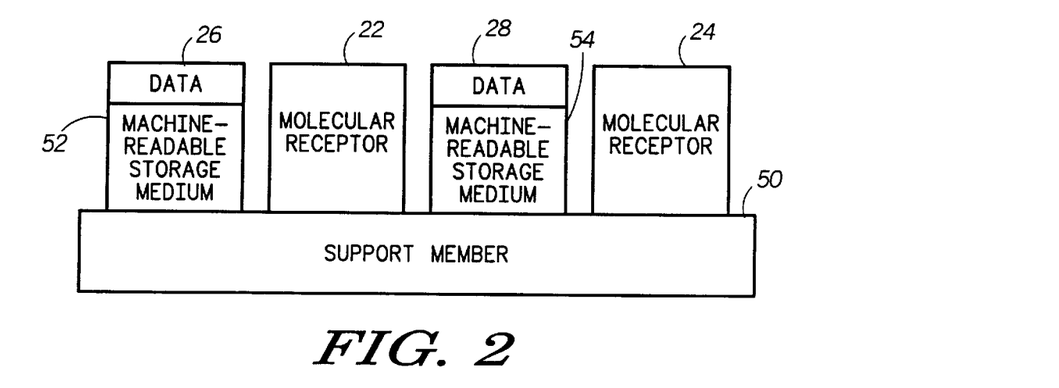
FIG. 2 is a block diagram of a first embodiment of the device.

FIG. 2 is a block diagram of a first embodiment of the device 20. In this embodiment, the device 20 includes a support member 50 to support the first molecular receptor 22, the second molecular receptor 24, the first machine-readable data 26, and the second machine-readable data 28. The support member 50 can be formed of various materials including semiconductive materials, conductive materials, and dielectric materials. Examples of preferred materials include, but are not limited to silicon, glass, metals, polymers, and plastics.

Preferably, the first molecular receptor 22, the second molecular receptor 24, the first machine-readable data 26, and the second machine-readable data 28 are attached to the support member 50. The molecular receptors 22 and 24 can be bound to a surface of the support member 50 using a primer, a gel, or an adhesive. Alternatively, the molecular receptors 22 and 24 can be integrated with a surface of the support member 50 using a molecular imprinting approach. As another alternative, like ones of the molecular receptors can be supported by a corresponding member placed on the surface. For example, molecular receptors can be contained in a prepatterned gel member placed on the surface.

Preferably, the first machine-readable data 26 is stored by a first machine-readable storage medium 52 supported by the support member 50. Similarly, it is preferred that the second machine readable data 28 be stored by a second machine-readable storage medium 54 supported by the support member 50. To store magnetic data, each of the machine-readable storage media 52 and 54 can include a magnetic storage medium. To store optical data, each of the machine-readable storage media 52 and 54 can include an optical storage medium.

Optionally, the first machine-readable storage medium 52 is adjacent the first molecular receptor 22, and the second machine-readable storage medium 54 is adjacent the second molecular receptor 22. Alternatively, the first machine-readable storage medium 52 is adjacent to the second machine-readable storage medium 54. In this case, the first molecular receptor 22 may or may not be adjacent the second molecular receptor 24.

Figure 3:
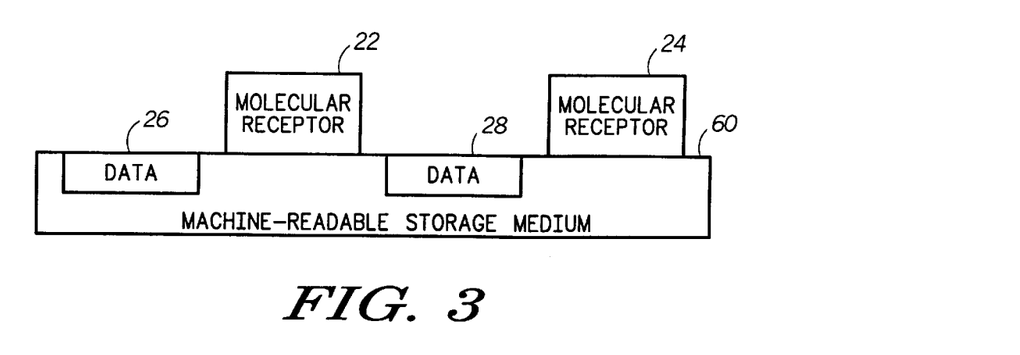
FIG. 3 is a block diagram of a second embodiment of the device.

FIG. 3 is a block diagram of a second embodiment of the device 20. In this embodiment, the device 20 includes a machine-readable storage medium 60 that supports the first molecular receptor 22 and the second molecular receptor 24. Examples of the machine-readable storage medium 60 include, but are not limited to, an optical storage medium such as CD-ROM, DVD, or other optical disk, and a magnetic storage medium such as a magnetic tape or a magnetic disk.

Preferably, the first molecular receptor 22 and the second molecular receptor 24 are attached to a surface of the machine-readable storage medium 60. The molecular receptors 22 and 24 can be bound to a surface of the machine-readable storage medium 60 using a primer, a gel, or an adhesive. Alternatively, the molecular receptors 22 and 24 can be integrated with a surface of the machine-readable storage medium 60 using a molecular imprinting approach. As another alternative, like ones of the molecular receptors can be supported by a corresponding member placed on the surface. For example, molecular receptors can be contained in a prepatterned gel member placed on the surface.

The machine-readable storage medium 60 stores the first machine-readable data 26 and the second machine-readable data 28. The first machine-readable data 26 is stored by a portion of the machine-readable storage medium 60 adjacent a portion which supports the first molecular receptor 22. The second machine-readable data 28 is stored by a portion of the machine-readable storage medium 60 adjacent to a portion which supports the second molecular receptor 24.

Optionally, the machine-readable storage medium 60 is also machine-writable. In this case, the machine-readable storage medium 60 can store machine-readable data associated with binding events at each binding site. For example, the machine-readable data can encode a qualitative or a quantitative indication of binding events occurring at each binding site.

Figure 4:
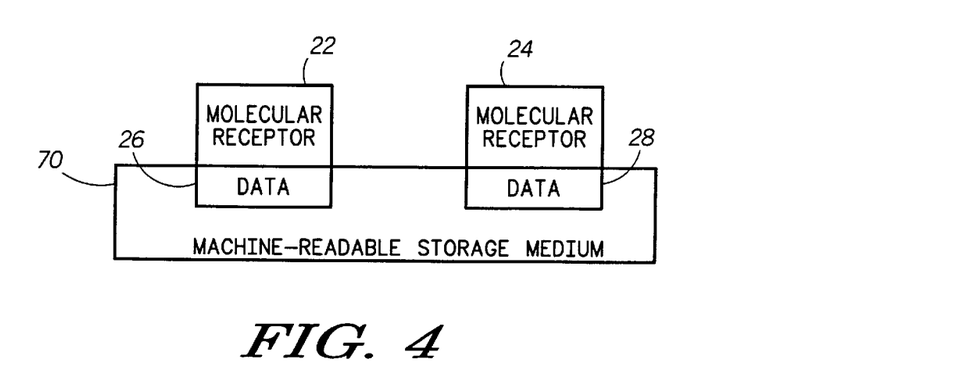
FIG. 4 is a block diagram of a third embodiment of the device.

FIG. 4 is a block diagram of a third embodiment of the device 20. The device 20 includes a machine-readable storage medium 70 that supports the first molecular receptor 22 and the second molecular receptor 24. Examples of the machine-readable storage medium 70 include, but are not limited to, an optical storage medium such as CD-ROM, DVD, or other optical disk, and a magnetic storage medium such as a magnetic tape or a magnetic disk. Preferably, the first molecular receptor 22 and the second molecular receptor 24 are attached to a surface of the machine-readable storage medium 70.

The machine-readable storage medium 70 stores the first machine-readable data 26 and the second machine-readable data 28. The first machine-readable data 26 is stored by a portion of the machine-readable storage medium 70 which supports the first molecular receptor 22. The second machine-readable data 28 is stored by a portion of the machine-readable storage medium 70 which supports the second molecular receptor 24. This configuration advantageously has the data co-located with its corresponding binding site.

Figure 5:
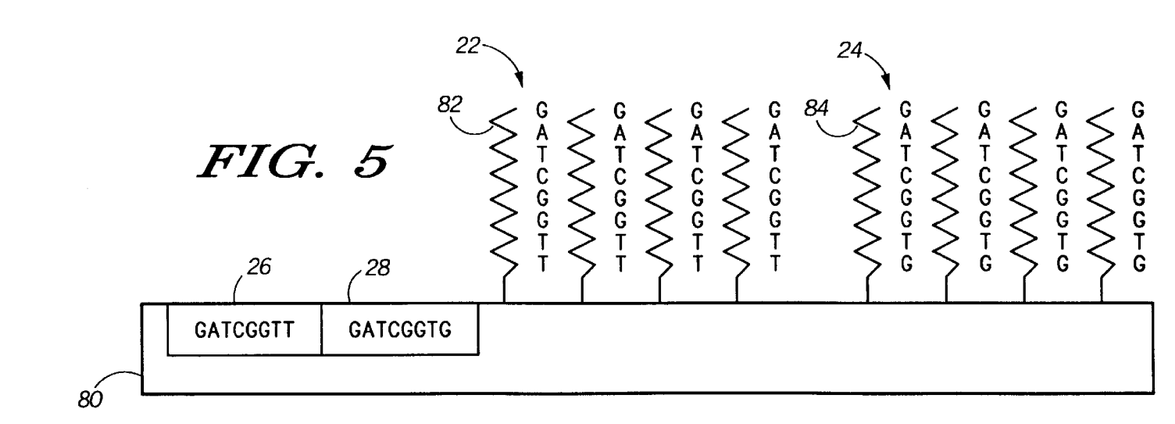
FIG. 5 is a schematic block diagram of an example of the device.

FIG. 5 is a schematic block diagram of an example of the device 20. The device 20 includes a member 80 which supports the first molecular receptor 22, the second molecular receptor 24, the first machine-readable data 26, and the second machine-readable data 28. The member 80 can include a support member as described with reference to FIG. 2 or a machine-readable storage medium as described with reference to FIGS. 3 and 4.

In this example, the first molecular receptor 22 comprises an oligonucleotide 82 bound to the member 80 at a first site. The second molecular receptor 24 comprises an oligonucleotide 84 bound to the member 80 at a second site. The oligonucleotides 82 and 84 are located at an assay portion of the member 80. For the purpose of illustration, the oligonucleotide 82 has a base sequence of G-A-T-C-G-G-T-T, and the oligonucleotide 84 has a base sequence of G-A-T-C-G-G-T-G.

The respective base sequence of each oligonucleotide is indicated using standard nucleotide abbreviations ("A" representing adenine, "C" representing cytosine, "G" representing guanine, "T" representing thymine). As is known in the art, each oligonucleotide specifically binds to molecules having a complementary sequence of nucleotide bases.

The first machine-readable data 26 encodes the base sequence of the oligonucleotide 82. The second machine-readable data 28 encodes the base sequence of the oligonucleotide 84. The first machine-readable data 26 and the second machine readable data 28 are located at a data portion of the member 80.

Figure 6:
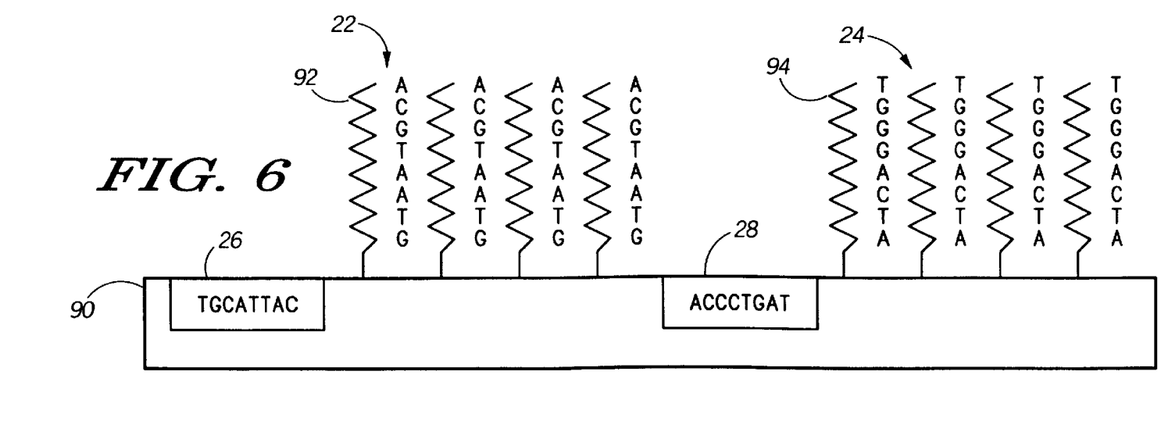
FIG. 6 is a schematic block diagram of another example of the device.

FIG. 6 is a schematic block diagram of another example of the device 20. The device 20 includes a member 90 which supports the first molecular receptor 22, the second molecular receptor 24, the first machine-readable data 26, and the second machine-readable data 28. The member 90 can include a support member as described with reference to FIG. 2 or a machine-readable storage medium as described with reference to FIGS. 3 and 4.

In this example, the first molecular receptor 22 comprises an oligonucleotide 92 bound to the member 90 at a first site. The second molecular receptor 24 comprises an oligonucleotide 94 bound to the member 80 at a second site. For the purpose of illustration, the oligonucleotide 92 has a base sequence of A-C-G-T-A-A-T-G, and the oligonucleotide 94 has a base sequence of T-G-G-G-A-C-T-A. The oligonucleotides 92 and 94 can be included with other oligonucleotides in a diagnostic array.

The first machine-readable data 26 encodes a base sequence complementary to the base sequence of the oligonucleotide 92. The second machine-readable data 28 encodes a base sequence complementary to the base sequence of the oligonucleotide 94. The first machine-readable data 26 is adjacent the oligonucleotide 92, and the second machine readable data 28 is adjacent the oligonucleotide 94.

Although the devices described with reference to FIGS. 1 to 6 are illustrated with two molecular receptors, it is noted that the teachings can be -extended for any number of molecular receptors. For example, devices which support a combinatorial array of oligonucleotides are contemplated, as are devices which support a plurality of molecular receptors specific to a plurality of disease sequences.

FIGS. 7 to 10 illustrate various embodiments of a preferred form of the device 20. In these embodiments, the device 20 includes a support member 100 having the form of a thin, circular disk. The support member 100 can include a support member as described with reference to FIG. 2 or a machine-readable storage medium as described with reference to FIGS. 3 and 4. The support member 100 includes a hub 102 which defines a hole 104. The hub 102 is for mounting the device 20 on a spindle or other like rotary positioning mechanism. If desired, the dimensions of the support member 100, the hub 102, and the hole 104 can be sized as a standard CD-ROM, a standard DVD, or any other disk-shaped storage medium.

The support member 100 supports a plurality of molecular receptors such as the molecular receptors 22 and 24 described with reference to FIG. 1, and machine-readable data such as the machine-readable data 26 and 28 described with reference to FIG. 1. The machine-readable data and the binding sites of the device 20 can be accessible from the same surface of the support member 100. Alternatively, the machine-readable data is readable from a surface of the support member 100 opposite to a surface from which the molecular receptors are accessible.

Figure 7:
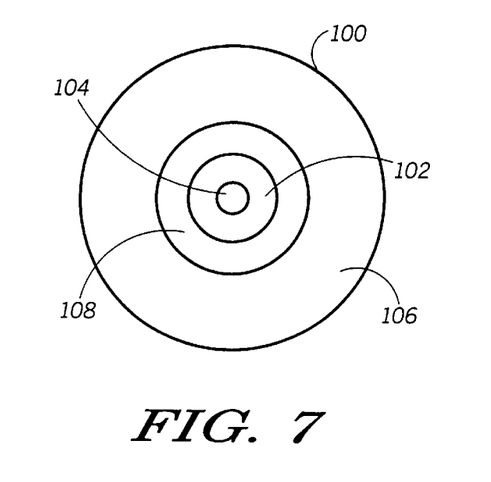
FIG. 7 is a plan view of a first embodiment of a disk-shaped device in accordance with the present invention.

FIG. 7 is a plan view of a first embodiment of a disk-shaped device in accordance with the present invention. In this embodiment, the support member 100 has a first annular portion 106 to support the binding sites (and hence the molecular receptors), and a second annular portion 108 to support the machine-readable data. The first annular portion 106 surrounds the second annular portion 108.

The binding sites can be arranged as a circular lattice within the first annular portion 106. In this case, the binding sites are distributed along one or more concentric rings within the first annular portion 106. Alternatively, the binding sites can be arranged as a spiral lattice within the first annular portion 106. In this case, the binding sites are distributed along a spiral within the first annular portion 106.

Similarly, the machine-readable data can be arranged as a circular lattice within the second annular portion 108. In this case, machine-readable data is distributed along one or more concentric rings within the second annular portion 108. Preferably, the rings are concentric with the concentric rings along which the binding sites are arranged.

Alternatively, the machine-readable data can be arranged as a spiral lattice within the second annular portion 108. In this case, the machine-readable data is distributed along a spiral within the second annular portion 108. Preferably, the machine-readable data and the binding sites are distributed along a common spiral.

Figure 8:
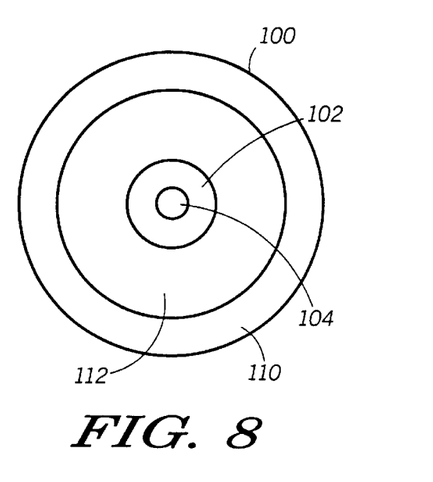
FIG. 8 is a plan view of a fourth embodiment of a disk-shaped device in accordance with the present invention.

FIG. 8 is a plan view of a second embodiment of a disk-shaped device in accordance with the present invention. The support member 100 has a first annular portion 110 to support binding sites having the molecular receptors, and a second annular portion 112 to support the machine-readable data. In this embodiment, the first annular portion 110 surrounds the second annular portion 112.

As with the embodiment of FIG. 7, the binding sites can be arranged either as a circular lattice or a spiral lattice within the first annular portion 110. The machine-readable data can be arranged either as a circular lattice or a spiral lattice within the second annular portion 112.

Figure 9:
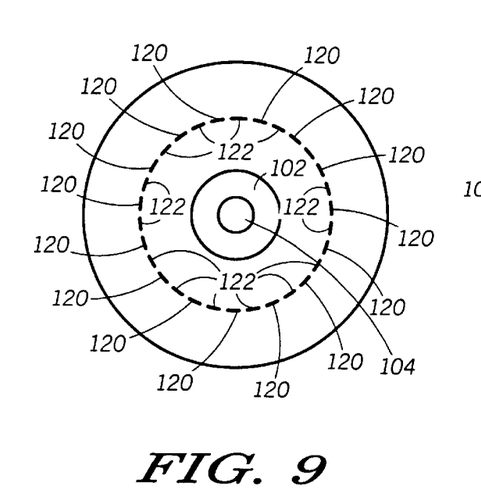
FIG. 9 is a plan view of a fourth embodiment of a disk-shaped device in accordance with the present invention.

FIG. 9 is a plan view of a third embodiment of a disk-shaped device in accordance with the present invention. In this embodiment, the support member 100 supports machine-readable data 120 interposed with binding sites 122. The machine-readable data 120 and the binding sites 122 can be arranged either in a circular lattice or in a spiral lattice.

The machine-readable data 120 is located between pairs of the binding sites 122 with respect to the lattice arrangement. Each of the machine-readable data items 120 identifies one or more of the binding sites 122 adjacent thereto.

Figure 10:
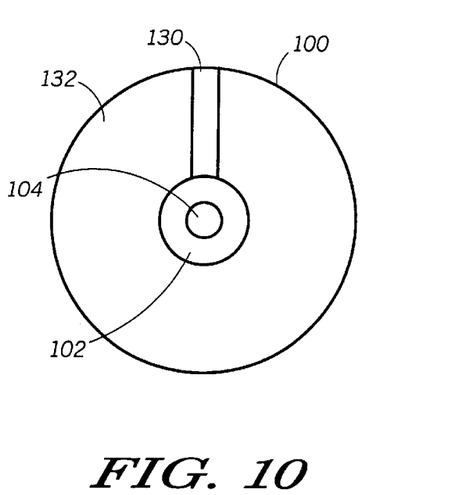
FIG. 10 is a plan view of a fourth embodiment of a disk-shaped device in accordance with the present invention.

FIG. 10 is a plan view of a fourth embodiment of a disk-shaped device in accordance with the present invention. In this embodiment, the support member 100 has a radial strip portion 130 to support the machine-readable data, and a remaining portion 132 to support the binding sites. Preferably, the binding sites and the machine-readable data are arranged either as a circular lattice or a spiral lattice. In this case, each resulting track of binding sites has a header of machine-readable data to identify the molecular receptors therein.

Figure 11:
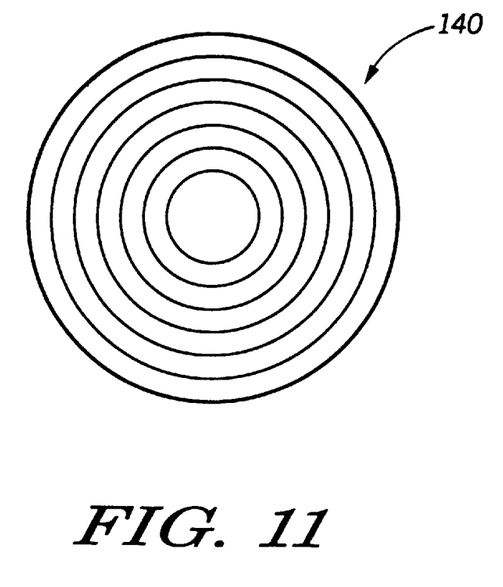
FIG. 11 illustrates an example of a circular lattice along which the machine-readable data and the binding sites can be arranged.

FIG. 11 illustrates an example of a circular lattice 140 along which the machine-readable data and the binding sites can be arranged. The circular lattice 140 is defined by a plurality of concentric rings. The machine-readable data and the binding sites are distributed either uniformly or nonuniformly along the concentric rings.

Figure 12:
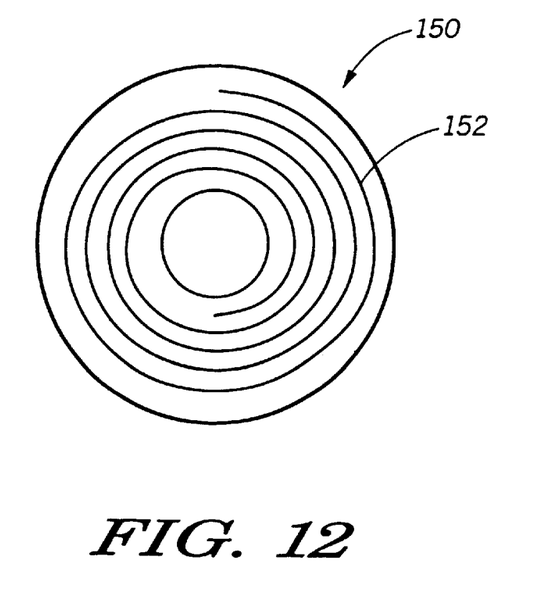
FIG. 12 illustrates an example of a spiral lattice along which the machine-readable data and the binding sites can be arranged.

FIG. 12 illustrates an example of a spiral lattice 150 along which the machine-readable data and the binding sites can be arranged. The spiral lattice 150 is defined by a spiral 152. The machine-readable data and the binding sites are distributed either uniformly or nonuniformly along the spiral 152.

Figure 13:
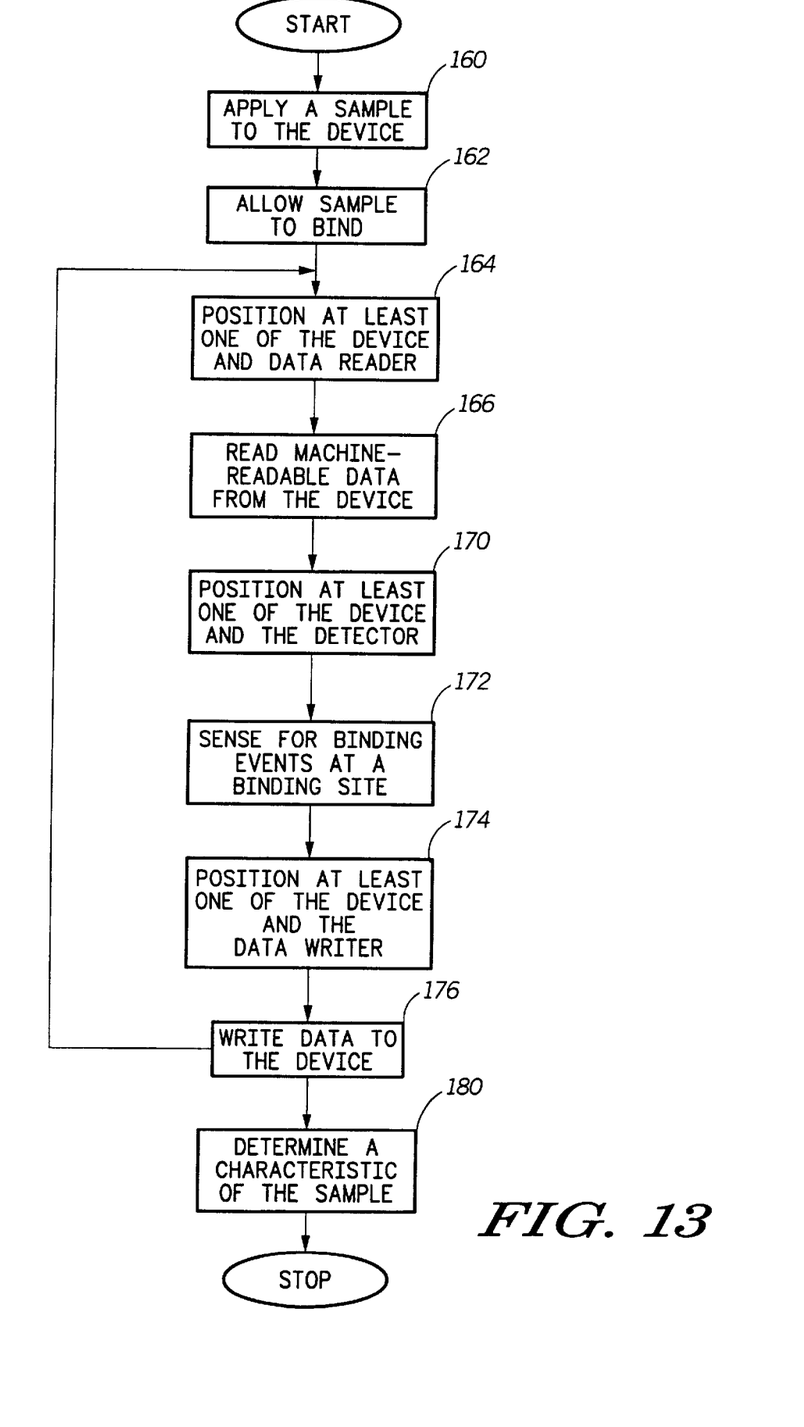
FIG. 13 is a flow chart of an embodiment of a molecular detection method in accordance with the present invention.

FIG. 13 is a flow chart of a molecular detection method in accordance with the present invention. As indicated by block 160, the method includes a step of applying a sample to the device 20 as described with reference to FIG. 1. Thereafter, the sample is allowed to bind or hybridize with the molecular receptors at the binding sites as indicated by block 162.

As indicated by block 164, the method includes a step of positioning at least one of the device 20 and the data reader 34. Preferably, the device 20 and/or the data reader 34 are positioned so that machine-readable data identifying a molecular receptor is accessible by the data reader 34. The step of positioning at least one of the device 20 and the data reader 34 can include translating the device 20, rotating the device 20, translating the data reader 34, and/or rotating the data reader 34. For disk-shaped embodiments of the device 20, the step of positioning preferably includes rotating the device 20 and radially translating a head of the data reader 34.

As indicated by block 166, the method includes a step of reading the machine-readable data from the device 20. The machine-readable data is read by the data reader 34.

As indicated by block 170, the method optionally includes a step of positioning at least one of the device 20 and the detector 38. Preferably, the device 20 and/or the detector 38 are positioned so that a binding event for a molecular receptor identified by the machine-readable data is detectable by the detector 38. The step of positioning at least one of the device 20 and the detector 38 can include translating the device 20, rotating the device 20, translating the detector 38, and/or rotating the detector 38. For disk-shaped embodiments of the device 20, the step of positioning preferably includes rotating the device 20 and radially translating a head of the detector 38.

As indicated by block 172, the method includes a step of sensing for binding events at the binding site. The binding events are sensed by the detector 38. The step of sensing produces binding data having either a qualitative indication or a quantitative indication of binding events occurring at the binding site. Examples of qualitative indications includes a positive detection indication and a negative detection indication of binding. Examples of quantitative indications include an intensity or a magnitude of binding at the binding site. The intensity can be indicative of a number of molecules bound at the binding site, a binding strength at the binding site, or a melting temperature at the binding site.

As indicated by block 174, the method optionally includes a step of positioning at least one of the device 20 and the data writer 40. Preferably, the device 20 and/or the data writer 40 are positioned so that a machine-writable storage medium is accessible by a head of the data writer 40. The step of positioning at least one of the device 20 and the data writer 40 can include translating the device 20, rotating the device 20, translating the data writer 40, and/or rotating the data writer 40. For disk-shaped embodiments of the device 20, the step of positioning preferably includes rotating the device 20 and radially translating a head of the data writer 40.

As indicated by block 176, the method optionally includes a step of writing data to the device 20. The data is written to the storage medium by the data writer 40. Preferably, the data is based upon binding data obtained from the detector 38.

It is noted that the steps indicated by blocks 164, 166, 170, 172, 174, and 176 need not be performed in the aforementioned order. Further, the aforementioned steps can be repeated to identify, sense binding data, and write binding data for additional binding sites of the device 20. The steps can be repeated to sequentially access binding sites or to randomly access binding sites.

As indicated by block 180, the method optionally includes a step of determining a characteristic of the sample based upon the binding data from at least one binding site.

The above-listed steps can be directed by the processor 36 described with reference to FIG. 1. The processor 36 can direct these steps based upon a software program or a firmware program stored by a computer-readable storage medium.

Thus, there has been described herein several embodiments including preferred embodiments of a binding assay.

Embodiments of the binding assay preferably and advantageously support molecular receptors, data identifying the molecular receptors and data associated with binding events for the molecular receptors.

It will be apparent to those skilled in the art that the disclosed invention may be modified in numerous ways and may assume many embodiments other than the preferred form specifically set out and described above. For example, it is noted that as an alternative to the disk-shaped embodiments of the binding assay, the binding assay can be supported by a magnetic tape within a cassette housing.

Accordingly, it is intended by the appended claims to cover all modifications of the invention which fall within the true spirit and scope of the invention.

What is claimed is:

1. An device comprising:
   an externally-readable, externally-writable, optical storage medium able to store machine readable data;
   a support member supporting machine readable data that is stored on said optical storage medium, said support member having a configuration selected from a group consisting of (a) concentric rings, and (b) a spiral;
   a plurality of molecular receptors supported at a first portion of the support member configuration; and
   machine readable data supported at a second portion of the support member configuration.

2. The device of claim 1, wherein said optical storage medium stores machine readable data identifying said plurality of molecular receptors; wherein a first machine readable data identifies a first molecular receptor; and a second machine readable data identifies a second molecular receptor.

3. The device of claim 1, wherein said support member has a configuration including at least a second annular portion surrounded by a concentric first annular portion.

4. The device of claim 1, wherein said support member has a configuration including at least a first annular portion and a second annular portion surrounded by said first annular portion.

5. The device of claim 2, wherein said first machine readable data identifies a base sequence of said first molecular receptor.

6. The device of claim 1, wherein said machine readable data identifies a plurality of base sequences associated with said the plurality of molecular receptors.

7. The device of claim 2, wherein said first molecular receptor binds to a first molecular structure.

8. The device of claim 1, wherein said plurality of molecular receptors hybridize to polynucleotides.

9. The device of claim 1, wherein said plurality of molecular receptors is arranged in a circular lattice.

10. The device of claim 1, wherein said plurality of molecular receptors is arranged in a spiral lattice.

11. The device of claim 2, wherein said first molecular receptor is attached to said optical storage medium.

12. The device of claim 1, wherein said support member is made from a material including at least one of silicon, glass, metal, polymer, and plastic.

13. The device of claim 1, wherein at least one molecular receptor is bound to a surface of said support member with a gel.

14. The device of claim 1, wherein at least one molecular receptor is bound to a surface of said support member with a primer.

15. The device of claim 1, wherein at least one molecular receptor is bound to a surface of said support member with an adhesive.

16. The device of claim 1, wherein at least one molecular receptor is integrated to a surface of said support member using an imprinting approach.

17. A system comprising the device of claim 1, and a data writer.

18. A system comprising the device of claim 1, and a detector.

19. A system comprising the device of claim 1, and a positioning mechanism.

* * * * *